United States Patent
Kadiyala et al.

(10) Patent No.: US 7,351,423 B2
(45) Date of Patent: Apr. 1, 2008

(54) MUSCULO-SKELETAL IMPLANT HAVING A BIOACTIVE GRADIENT

(75) Inventors: Sudhakar Kadiyala, Newton, MA (US); Francois Binette, Weymouth, MA (US); Cynthia Marie Coleman, Brookline, MA (US); Theresa Adams Kapur, Stoughton, MA (US)

(73) Assignee: Depuy Spine, Inc., Raynham, MA (US)

( * ) Notice: Subject to any disclaimer, the term of this patent is extended or adjusted under 35 U.S.C. 154(b) by 10 days.

(21) Appl. No.: 11/189,691

(22) Filed: Jul. 26, 2005

(65) Prior Publication Data

US 2006/0045903 A1   Mar. 2, 2006

Related U.S. Application Data

(60) Provisional application No. 60/606,382, filed on Sep. 1, 2004.

(51) Int. Cl.
  *A61F 2/00* (2006.01)
(52) U.S. Cl. ....................................................... 424/426
(58) Field of Classification Search ................. 424/426
  See application file for complete search history.

(56) References Cited

U.S. PATENT DOCUMENTS

| | | | |
|---|---|---|---|
| 5,041,138 A * | 8/1991 | Vacanti et al. ............... | 424/422 |
| 5,133,755 A * | 7/1992 | Brekke ..................... | 623/23.51 |
| 5,368,858 A | 11/1994 | Hunziker | |
| 5,716,404 A | 2/1998 | Vacanti et al. | |
| 5,843,156 A | 12/1998 | Slepian et al. | |
| 5,853,753 A | 12/1998 | Maierhofer et al. | |
| 5,855,610 A | 1/1999 | Vacanti et al. | |
| 5,900,433 A | 5/1999 | Igo et al. | |
| 6,123,727 A | 9/2000 | Vacanti et al. | |
| 6,281,015 B1 | 8/2001 | Mooney et al. | |
| 6,290,729 B1 | 9/2001 | Slepian et al. | |
| 6,448,054 B1 | 9/2002 | Poznansky et al. | |
| 6,454,811 B1 | 9/2002 | Sherwood et al. | |
| 6,468,731 B1 | 10/2002 | Hubbell et al. | |
| 6,596,296 B1 * | 7/2003 | Nelson et al. .............. | 424/426 |
| 6,656,488 B2 | 12/2003 | Yi et al. | |
| 6,656,496 B1 | 12/2003 | Kilpadi et al. | |
| 6,685,957 B1 | 2/2004 | Bezemer et al. | |
| 6,852,330 B2 * | 2/2005 | Bowman et al. ............. | 424/426 |
| 7,115,280 B2 * | 10/2006 | Hanna et al. ................ | 424/489 |
| 2002/0032488 A1 | 3/2002 | Brekke et al. | |
| 2002/0127265 A1 | 9/2002 | Bowman et al. | |

(Continued)

FOREIGN PATENT DOCUMENTS

EP      1 090 928 B1     9/2000

(Continued)

OTHER PUBLICATIONS

Davisdon et al., Effect of Perfusion on the Growth of Tissue Engineered Cartilage, Orthopaedic Research Society, 1999, p. 811.

(Continued)

*Primary Examiner*—Sharon Kennedy
(74) *Attorney, Agent, or Firm*—Thomas M. DiMauro

(57) ABSTRACT

This invention relates to an implant for a musculoskeletal defect having a bioactive agent having a concentration gradient.

24 Claims, 16 Drawing Sheets

U.S. PATENT DOCUMENTS

| | | |
|---|---|---|
| 2002/0150753 A1 | 10/2002 | Me et al. |
| 2002/0183858 A1 | 12/2002 | Contiliano et al. |
| 2003/0012818 A1 | 1/2003 | Schense et al. |
| 2003/0017141 A1 | 1/2003 | Poznnansky et al. |
| 2003/0022153 A1 | 1/2003 | Kirk et al. |
| 2003/0022197 A1 | 1/2003 | Kirk et al. |
| 2003/0022269 A1 | 1/2003 | Kirk et al. |
| 2003/0022362 A1 | 1/2003 | Kirk et al. |
| 2003/0036193 A1 | 2/2003 | Fallon et al. |
| 2003/0045943 A1 | 3/2003 | Brekke et al. |
| 2003/0099762 A1* | 5/2003 | Zhang et al. ............ 427/2.1 |
| 2003/0114936 A1 | 6/2003 | Sherwood et al. |
| 2003/0143258 A1 | 7/2003 | Knaack et al. |
| 2003/0147935 A1 | 8/2003 | Binette et al. |
| 2003/0166833 A1 | 9/2003 | Lutolf et al. |
| 2003/0187232 A1 | 10/2003 | Hubbell et al. |
| 2003/0199440 A1 | 10/2003 | Dack et al. |
| 2004/0002131 A1 | 1/2004 | Kim et al. |
| 2004/0028739 A1 | 2/2004 | Ripon et al. |
| 2004/0132143 A1 | 7/2004 | DeAngelis et al. |
| 2004/0142411 A1 | 7/2004 | Kirk et al. |

FOREIGN PATENT DOCUMENTS

| | | |
|---|---|---|
| EP | 0 794 790 B1 | 4/2002 |
| EP | 1 264 607 A1 | 12/2002 |
| EP | 1 098 684 B1 | 8/2003 |
| EP | 1 346 731 A1 | 9/2003 |
| EP | 1 407 791 A1 | 4/2004 |
| EP | 1 416 044 A1 | 6/2004 |
| WO | WO 95/09659 A1 | 4/1995 |
| WO | WO 00/51538 A1 | 9/2000 |
| WO | WO 01/38428 A1 | 5/2001 |
| WO | WO 01/70293 A1 | 9/2001 |
| WO | WO 01/83522 A2 | 11/2001 |
| WO | WO 01/85845 A1 | 11/2001 |
| WO | WO 02/15955 A2 | 2/2002 |
| WO | WO 02/062968 A2 | 8/2002 |
| WO | WO 02/085422 A1 | 10/2002 |
| WO | WO 02/100426 A1 | 12/2002 |
| WO | WO 03026674 A1 | 4/2003 |
| WO | WO 03030956 A2 | 4/2003 |
| WO | WO 03052091 A1 | 6/2003 |
| WO | WO 03/070186 A2 | 8/2003 |
| WO | WO 03/078565 A1 | 9/2003 |
| WO | WO 03103573 A2 | 12/2003 |
| WO | WO 04032830 A2 | 4/2004 |
| WO | WO 04032988 A2 | 4/2004 |
| WO | WO 2004/038367 A2 | 5/2004 |
| WO | WO 2004/053165 A1 | 6/2004 |

OTHER PUBLICATIONS

Raudenbush et al., Subchondral Thickness Does Not Vary With Cartilage Degeneration on the Metatarsal, Journal of the American Podiatric Medical Association, Mar./Apr. 2003, pp. 104-110, vol. 93, No. 2.

Glowacki et al., Perfusion Enhances Functions of Bone Marrow Stromal Cells in Three-Dimensional Culture, Cell Transplantation, 1998, pp. 319-326, vol. 7, No. 3, Elsevier Science, Inc.

Bujia et al., Engineering of Cartilage Tissue Using Bioresorbable Polymer Fleeces and Perfusion Culture, Acta Otolaryngol, 1995, pp. 301-310, vol. 115, Scandinavian University Press.

Freed et al., Cultivation of Cell-Polymer Cartilage Implants in Bioreactors, Journal of Cellular Biochemistry, 1993, pp. 257-264, vol. 51, Wiley Liss, Inc.

Levin et al., Osteoarthritis-like Disorder in Rats with vascular Deprivation—induced Necrosis of the Femoral Head, Pathology Research and Practice, 1999, pp. 637-647, vol. 195, Urban & Fischer Verlag.

Sittinger et al., Engineering of Cartilage Tissue Using Bioresorbable Polymer Carries in Perfusion Culture, Biomaterials, 1994, pp. 451-456, vol. 15, No. 6, Butterworth-Heinemann Ltd.

Honner et al., The Nutritional Pathways of Articular Cartilage, The Journal of Bone and Joint Surgery, Jun. 1974, pp. 742-748, vol. 53A, No. 4.

Lajeunesse et al., "The Role of Bone in The Treatment of Osteoarthritis", Osteoarthritis and Cartilage, 2004, pp. 34-38, vol. 12, Elsevier Ltd.

Kapur et al., "Immobilized Concentration Gradients of Nerve Growth Factor Guide Neurite Outgrowth", Wikey IinterScience, 2003, pp. 235-243, Wiley Periodicals.

Hypolite et al., Formation of Microscale Gradients of Protein Using Heterobifunctional Photolinkers, Bioconjungate Chem., 1997, pp. 658-663, vol. 8, American Chemical Society.

Ito et al., "Gradient Micropattern Immobilization of Heparin and Its Interaction with Cells", Journal of Biomaterial Science Polymer Edition, 2001, pp. 367-378, vol. 12, No. 4.

Cao et al., Defining the Concentration Gradient of Nerve Growth Factor For Guided Neurite Outgrowth, Neuroscience,2001, pp. 831-840, vol. 103, No. 3, Elsevier Science Ltd.

Mahewhwari et al., "Cell Adhesion and Motility Depend on Nanoscale RGD Clustering", Journal of Cell Science, 2000, pp. 1677-1686, vol. 113, The Company of Biologistics Limited.

Gallo et al., "The trkA Receptor Mediates Growth Cone Turning Toward A Localized Source of Nerve Growth Factor", The Journal of Neuroscience, Jul. 15, 1997, pp. 5445-5454, vol. 14, No. 14, Society for Neruoscience.

Kuffler et al., Guidance of Regenerating Motor Axons in Vivo By Gradients of Diffusible Perpheral Nerve-Derived Factors, Journal of Neurobiology, Feb. 2000, pp. 212-219, vol. 42, No. 2.

Baier et al., "Axon Guidance by Gradients of a Target-Derived Component", Science, Jan. 24, 1992, pp. 472-475, vol. 255, issue 5043, American Association For The Advancement of Science.

Snow et al., Neurite Outgrowth on a Step Gradient of Chondrotin Sulfate Proteoglycan (CS-PG), Journal of Neurobiology, 1992, pp. 322-336, vol. 23.

Flurkey, "An Inexpensive Gradient Make for the Biochemistry Laboratory", Journal of Chemical Education, Aug. 2000, pp. 1041-, vol. 77, Issue 8, American Chemical Society.

Iwasaki et al., "The Effect of The Chemical Structure of the Phospholipid Polymer on Fibronectin Adsorption and Fibroblast Adhesion on the Gradient Phospholipid Surface", Biomaterials, 1999, pp. 2185-2191, vol. 20, Elsevier Science Ltd.

Rosentreter et al., Response of Retinal Ganglion Cell Axons to Striped Linear Gradients of Repellent Guidance Molecules, Journal of Neurobiology, 1998, pp. 541-562, vol. 37, John Wiley & Sons, Inc.

Halfter et al., "The Behavior of Optic Axons on Substrate Gradients of Retinal Basal Lamina Proteins and Merosin", Journal of Neuroscience, Jul. 15, 1996, pp. 4389-4401, vol. 16, No. 14, Society of Neuroscience.

Zheng et al., Guidance of Regenerating Motor Axons In Vivo by Gradients of Diffusible Peripheral Nerve-Derived Factors, Journal of Neruobiology, 2000, pp. 212-279, vol. 42, John Wiley & Sons.

* cited by examiner

FIG. 4C
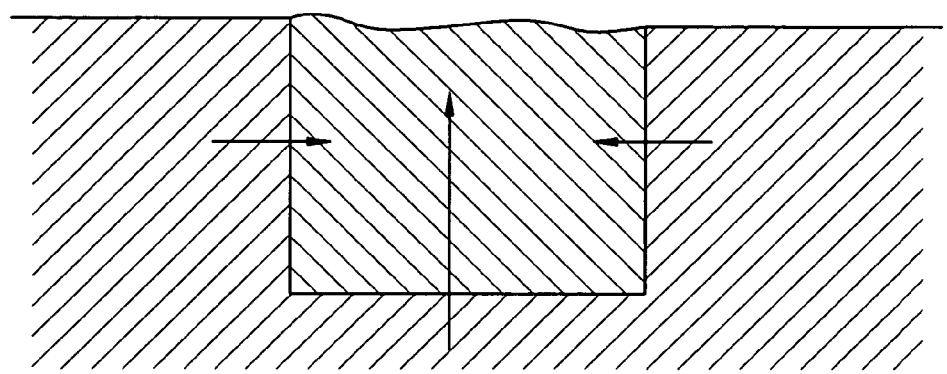
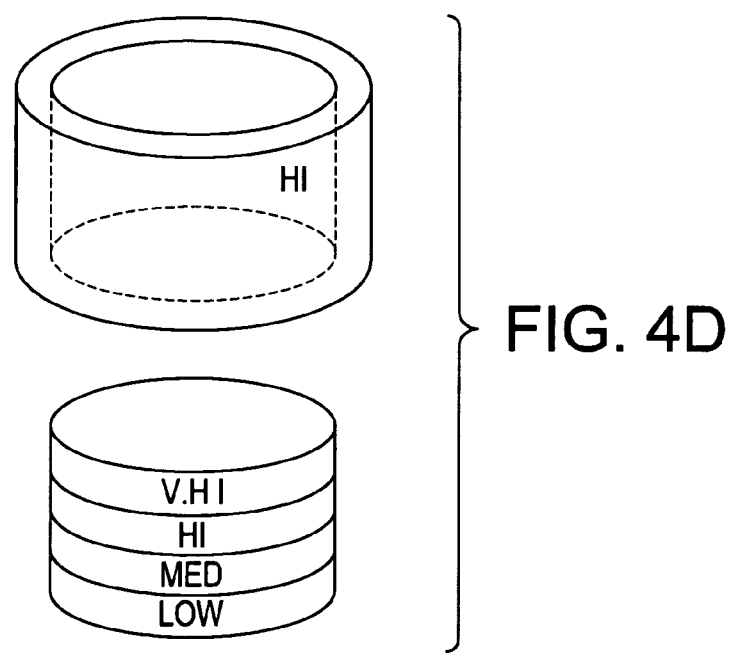
FIG. 4D

DIFFERENTIATION

MUSCULO-SKELETAL IMPLANT HAVING A BIOACTIVE GRADIENT

CONTINUING DATA

This application claims the benefit of U.S. Provisional Patent Application Ser. No. 60/606,382, entitled "Musculo-Skeletal Implant Having a Bioactive Gradient", filed Sept. 1, 2004, the specification of which is incorporated by reference in its entirety.

FIELD OF THE INVENTION

The present invention relates to biocompatible tissue implant devices for use in the repair of tissue injuries, organ disease states and/or congenital anomalies as well as methods for making and using such biocompatible tissue implant devices.

BACKGROUND OF THE INVENTION

Injuries to tissue, such as cartilage, meniscus, intervertebral disc, skin, muscle, bone, tendon and ligament, where the tissue has been injured or traumatized, frequently require surgical intervention to repair the damage and facilitate healing. Such surgical repairs can include suturing or otherwise repairing the damaged tissue with known medical devices, augmenting the damaged tissue with other tissue, using an implant or a graft or any combination of these techniques.

One common tissue injury involves damage to cartilage, which is a non-vascular, resilient, flexible elastic connective tissue. Cartilage typically acts as a "shock-absorber" at articulating joints, but some types of cartilage provide support to tubular structures, such as for example, the larynx, air passages, and the ears. In general, cartilage tissue is comprised of cartilage cells, known as chondrocytes, located in an extracellular matrix, which contains collagen, a structural scaffold, and aggrecan, a space-filling proteoglycan. Several types of cartilage can be found in the body, including hyaline cartilage, fibrocartilage and elastic cartilage. Hyaline cartilage can appear in the body as distinct pieces, or alternatively, this type of cartilage can be found fused to the articular ends of bones. Hyaline cartilage is generally found in the body as articular cartilage, costal cartilage, and temporary cartilage (i.e., cartilage that is ultimately replaced by bone through the process of ossification). Fibrocartilage is a transitional tissue that is typically located between tendon and bone, bone and bone, and/or hyaline cartilage and hyaline cartilage. Elastic cartilage, which contains elastic fibers distributed throughout the extracellular matrix, is typically found in the epiglottis, the ears and the nose.

One common example of hyaline cartilage injury is a traumatic focal articular cartilage defect to the knee. A strong impact to the joint can result in the complete or partial removal of a cartilage fragment of variable size and shape. Damaged articular cartilage can severely restrict joint function, cause debilitating pain and may result in long term chronic diseases such as osteoarthritis, which gradually destroys the cartilage and underlying bone of the joint. Injuries to the articular cartilage tissue will not heal spontaneously and require surgical intervention if symptomatic. A modality of treatment consists of debridement and the removal of partially or completely unattached tissue fragments. In addition, the surgeon will often use a variety of methods such as abrasion, drilling or microfractures, to induce bleeding into the cartilage defect and formation of a clot. It is believed that the cells coming from the marrow will form a scar-like tissue, fibrocartilage, which can provide temporary relief to some symptoms. Unfortunately, fibrocartilage does not have the same mechanical properties as hyaline cartilage and degrades over time as a consequence of wear. Patients typically have to undergo repeated surgical procedures, which can lead to the complete deterioration of the cartilage surface. More recently, experimental approaches involving the implantation of autologous chondrocytes have been used with increasing frequency. The process involves the harvest of a small piece of articular cartilage in a first surgical procedure, which is then transported to a laboratory specialized in cell culture for amplification. The tissue piece is treated with enzymes that will release the chondrocytes from the matrix, and the isolated cells will be grown for a period of 3 to 4 weeks using standard tissue culture techniques. Once the cell population has reached a target number, the cells are sent back to the surgeon for implantation during a second surgical procedure. This manual, labor-intensive process is extremely costly and time consuming. Although the clinical data suggest long-term benefit for the patient, the prohibitive cost of the operation combined with the traumatic impact of two surgical procedures to the knee, have hampered adoption of this technique.

U.S. Pat. No. 5,368,858 ("Hunziker") discloses compositions for the treatment and repair of cartilage defects. To induce cartilage formation, the defect is filled or otherwise dressed with a biodegradable matrix having pores sufficiently large to allow repair cells to populate the matrix. The matrix filling the defect contains a proliferation agent at a concentration sufficient to stimulate proliferation of repair cells and a transforming factor in an appropriate delivery system that releases the transforming factor at a concentration sufficient to transform repair cells in the matrix and defect area into cartilage-producing chondrocytes. The matrix may also contain a chemotactic agent to attract repair cells. The entire treatment may be carried out in a single arthroscopic or open surgical procedure.

Hunziker does not teach using cartilage derived morphogenetic proteins (CDMPs) or growth differentiation factors (GDFs) as exogenous bioactive agents.

SUMMARY OF THE INVENTION

The present inventors have recognized that prior art implants routinely provide bioactive agents in a relatively homogenous concentration throughout the implant scaffold. Such a conventional implant is shown in FIG. 12. At time $T_0$, the concentration of the bioactive agent is homogenous through the implant. At time $T_1$, the diffusion of the bioactive agent out of the implant leads to a concentration gradient in the implant. Accordingly, although cells C in the adjacent native tissue may respond to such a gradient chemotactically, these cells C would be provided with a significant chemotactic environment, but only up to the edge E of the implant, as any gradient becomes insubstantial within the implant. Accordingly, any chemotactic affect provided by the bioactive agent would not result a substantial amount of cells entering the bulk of the implant. Accordingly, a homogeneously loaded implant likely produces only incomplete infiltration throughout the implant.

It is believed that the musculoskeletal repair process may be further enhanced by providing an implant that provides bioactive agents (such as rhGDF-5) to the cellular environment of the implant in a manner that more fully exploits the bioactive agent's characteristics (such as chemotaxis) in a more desirable manner. It is further believed that specifically grading the spatial concentration of a bioactive agent within the implant may provide effects from the bioactive agent that would be superior to implants having a homogeneous agent concentration profile.

Accordingly, in some embodiments, the implant includes a bioactive agent presented to the cellular environment in a concentration profile characterized by a spatial gradient. Without wishing to be tied to a theory, it is believed that the musculoskeletal repair process may be further accelerated or enhanced by providing a spatially-graded bioactive agent concentration within the cellular environment of the implant that enhances the chemotactic properties of the bioactive agent.

Therefore, in accordance with the present invention, there is provided an implant for repair of an musculoskeletal defect, comprising:

a) a matrix having a central region, an upper region, a lower region and a peripheral region, and
b) a bioactive agent present within the matrix, wherein the presence of the bioactive agent in the matrix is characterized by a controlled spatial concentration gradient.

In another aspect of the present invention, the implant includes bioactive agents presented to the cellular environment via two different matrix phases of the implant, wherein at least one of the bioactive agents is a member of the BMP superfamily, preferably a GDF, more preferably rhGDF-5. In some embodiments thereof, the first and second phases respectively contain rhGDF-5 and a different bioactive agent. In others, the two phases contain the same rhGDF-5 bioactive agent but at different or similar concentrations. Desirably, the two phases are designed to release the bioactive agents to the cellular environment at different times, thereby allowing the bioactive agents to spur different phases of regeneration or repair. It is believed that specifically tailoring the timing of the release of the bioactive agent(s) within the implant may provide effects from the agent that would be superior to implants having a single, unimodal release profile.

Therefore, in accordance with the present invention, there is provided an implant for repair of an musculoskeletal defect, comprising:

a) a matrix, and
b) a first phase containing a first bioactive agent adapted to provide a first concentration to a cellular environment, and
c) a second phase containing a second bioactive agent adapted to provide a second concentration to a cellular environment, wherein at least one of the bioactive agents is a GDF.

Preferably, in the dual phase aspect of the novel implant, the bioactive agent associated with the first phase enhances at least one of chemotaxis and proliferation, while the bioactive agent associated with the second phase enhances at least one of differentiation and ECM stimulation. Such an implant would allow the migration and proliferation of native cells into the implant without their premature differentiation. Avoiding premature differentiation of these native cells is advantageous because it allows the cells to migrate, resulting in appropriate cellular distribution through the implant.

DESCRIPTION OF THE FIGURES

FIGS. 1, 2a, 3a, 4a, 4c, 5a are cross-sections of implants of the present invention implanted in musculoskeletal defects and having concentration gradients of a bioactive factor.

FIG. 4d depicts an implant of the present invention having an axially varying and a laterally varying spatial concentration gradient of a bioactive factor.

DETAILED DESCRIPTION

For the purposes of the present invention, a "matrix" is interchangeable with a "carrier". "Presented to the cellular environment" means "not sequestered" or "sequestered, then released" or "sequestered".

A "bioactive agent" or "agent" is a protein (for example, ECM molecules, growth factors, signaling molecules, etc), gene, small molecule, DNA or RNA fragment, peptide, virus, sugar or mineral.

The term "chemotaxis" is intended to include hepatotaxic effects and movements.

It is believed that designing an implant to possess a spatially-graded chemotactic factor concentration profile can be beneficial in two ways. First, the resulting chemotaxis could enhance the uniform distribution of viable cells within the implant. Second, it could enhance tissue integration with the surrounding native tissue.

It is often the case that an implant contains either no cells or cells present only upon an outer surface of the implant. In such cases, a chemotactic bioactive agent may be used to insure that the influx of cells into the bulk of the implant proceeds in a way that provides cellular homogeneity throughout the implant.

Similarly, it is known that integration of regenerated musculoskeletal tissue with the neighboring mature tissue is often problematic. It is believed that integration of these two tissues may be enhanced by simply increasing the amount of cells migrating from the mature tissue into the implant area. Accordingly, in some embodiments, a chemotactic bioactive agent is provided in the implant in a spatial distribution adapted to increase the amount of cells migrating from the mature tissue into the region adjacent the implant area.

Figure 1:
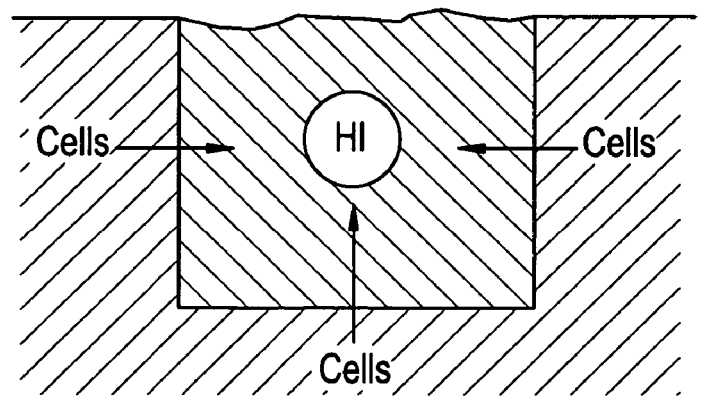

Now referring to FIG. 1, there is provided a biocompatible implant wherein the chemotactic bioactive is presented to the cellular environment in a relatively high concentration HI in its central region. Under these conditions, the viable cells from the neighboring mature tissue will be signaled by the chemotactic concentration gradient to vigorously migrate towards the center of the implant, thereby promoting uniform cellular distribution. This embodiment is particularly useful in implants that are implanted with relatively inactive cells or no active cells, in that the desired chemotactic effect will produce an ingress of viable cells from all directions towards the center of the implant, not just the implant periphery.

The chemotactic profile of FIG. 1 can be produced by first forming a porous spherical body (such as a granule) having a uniform concentration of the chemotactic factor therein, and the coating that sphere with a porous coating or foam.

Figure 2A:
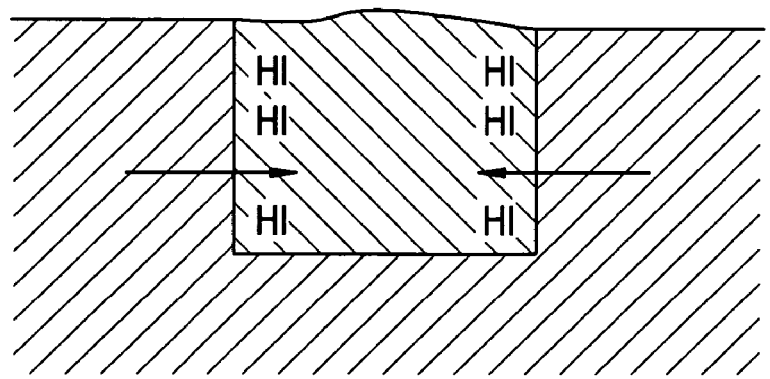

Now referring to FIG. 2a, there is provided a biocompatible implant wherein the chemotactic bioactive is presented to the cellular environment in a relatively high concentration, but only in its peripheral region. As the bioactive agent begins to diffuse and spatially spread over time, the diffusion will create a local gradient having a maximum in the peripheral region. Under these conditions, the cells from the neighboring mature tissue will be signaled by the chemotactic concentration gradient to migrate from the native tissue bulk to the edge region of the native tissue and into peripheral region of the implant. Once the cells have migrated into these neighboring regions, they may be stimulated to excrete extracellular matrix, thereby promoting tissue integration.

This embodiment may also be useful when implants have a large amount of viable cells. In some embodiments, providing a high concentration of active agent only at the periphery of the implant may, after diffusion of the bioactive agent into neighboring areas, promote a partial efflux of cells from the implant into an adjacent native tissue region. Since the adjacent native tissue region may contain only relatively inactive cells, the efflux of viable cells from the implant may prove beneficial. In such a case, the emigrating cells can produce ECM in that adjacent region, thereby promoting tissue integration.

Figure 2B:
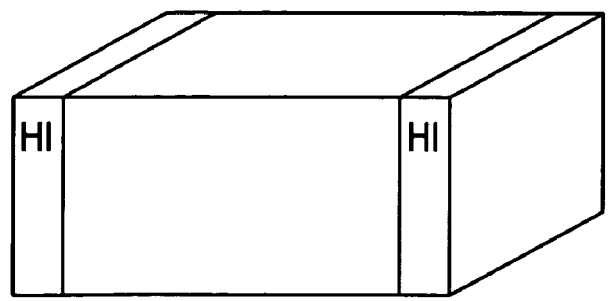
FIGS. 2b and 2c depict implants for a musculoskeletal defect having peripheral spatial concentration gradients of a bioactive factor.

Now referring to FIG. 2b, the chemotactic profile of FIG. 2a can be produced by coating the radial edges of a porous scaffold with a coating having a high concentration of a chemotactic agent contained therein.

Figure 2C:
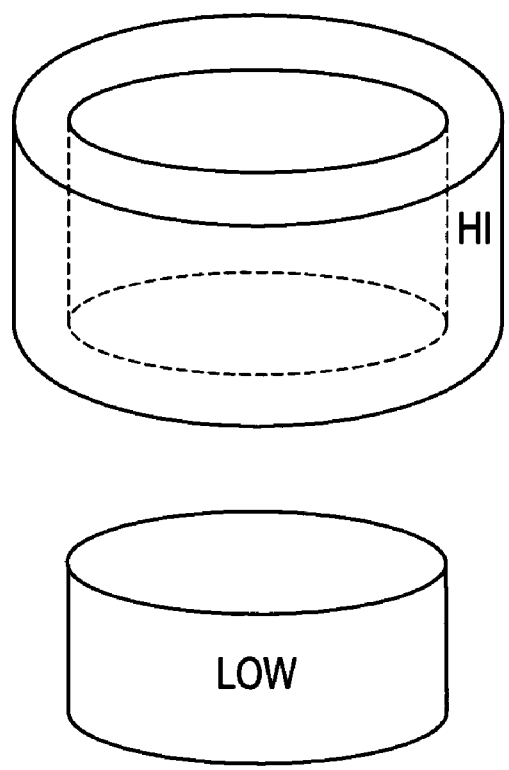

Now referring to FIG. 2c, the chemotactic profile of FIG. 1 can be produced by fitting an annular scaffold containing a HI concentration of the bioactive agent around a cylindrical plug containing a low concentration of the agent.

Figure 3A:
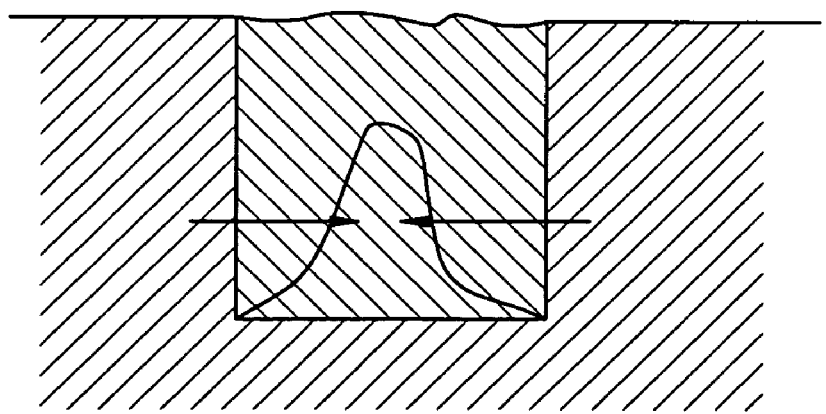

Now referring to FIG. 3a, there is provided a biocompatible implant wherein the chemotactic bioactive agent presented to the cellular environment has a high concentration in the central axial region, and a lower concentration in the peripheral regions, so that it is graded in the X-direction. Under these conditions, the cells from the neighboring mature cartilage tissue will be signaled by the chemotactic concentration gradient to migrate towards the center axis of the implant, thereby promoting cellular uniformity. This embodiment is particularly useful in implants that are implanted with relatively inactive cells or no active cells, in that chemotactic effect is produced across the border of the neighboring native tissue.

The chemotactic profile of FIG. 3a can be produced by a) providing multiple slices of scaffold, with each slice presenting a different chemotactic factor concentration to the cellular environment, and b) arranging those slices vertically to produce the scaffold having the desired spatial gradient. In some embodiments, successive slices of scaffold having low, high and low concentrations of chemotactic bioactive agent are joined together.

Figure 3B:
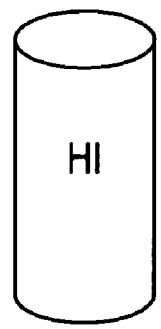
FIG. 3b depicts an implant of the present invention having a laterally varying spatial concentration gradient of a bioactive factor.
Figure 3B:
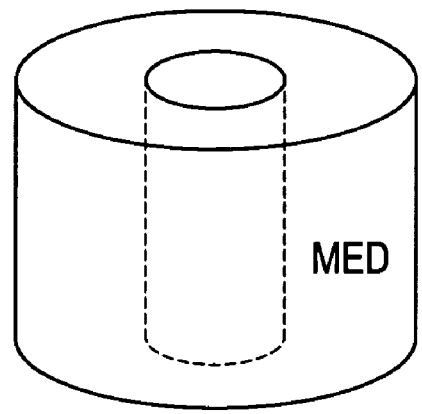
Figure 3B:
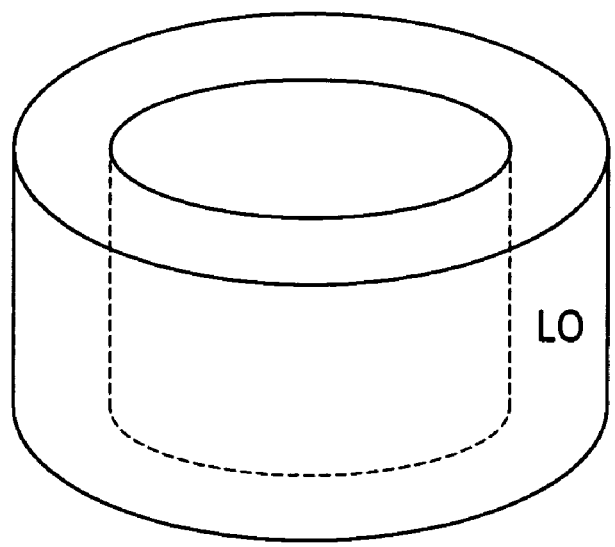

Alternatively, and now referring to FIG. 3b, the chemotactic profile of FIG. 3a can be produced by assembling a central dowel having a HI concentration of the bioactive agent, an intermediate annulus having a medium MED concentration, and an outer annulus having a LO concentration of the bioactive agent.

Figure 4A:
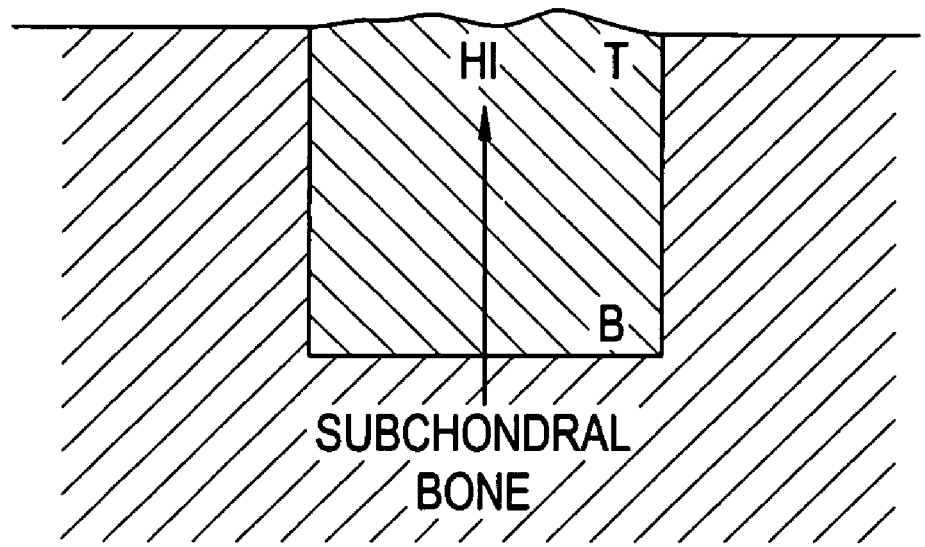

Now referring to FIG. 4a, there is provided a biocompatible implant wherein the chemotactic agent is presented to the cellular environment in a relatively high concentration near the top of the implant, near the synovial fluid. Under these conditions, the cells present near the bottom B of the implant will be signaled by the chemotactic concentration gradient to migrate towards the top T of the implant, thereby promoting cellular uniform cellular distribution throughout the implant.

The spatial gradient of FIG. 4a may be useful in at least two situations. In the first, a surface of the implant is coated with a cellular layer (adjacent region B), and the implant is implanted with the cell-coated surface abutting the subchondral bone.

In the second, the implant is substantially cell-free and the subchondral bone is pierced just prior to implantation of the implant, thereby allowing an influx of bone marrow containing stem cells into the implant. In each case, the spatial gradient assists in the upward migration of cells from the bottom B of the implant.

Providing a coating containing a chemotactic factor upon the upper surface of the scaffold can produce the chemotactic profile of FIG. 4a.

Figure 4B:
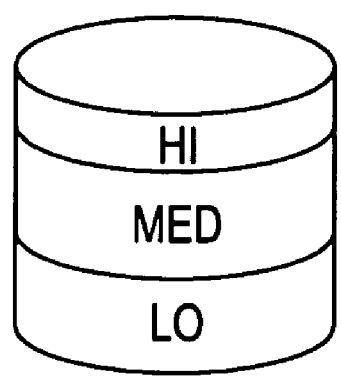
FIGS. 4b and 5b depict implants of the present invention having an axially varying spatial concentration gradient of a bioactive factor.

Now referring to FIG. 4b, the chemotactic profile of FIG. 4a can also be produced by providing successive layers of scaffold having increasing bioactive agent concentrations from the bottom (LO) to the top(HI).

In some instances, and now referring to FIG. 4c, both vertical migration of cells and enhanced peripheral tissue integration are desired. Therefore, the implant of FIG. 4c may be designed to provide each of these qualities.

Now therefore, and now referring to FIG. 4d, in some embodiments, the implant may comprises an outer annulus having a HI concentration of the chemotactic factor and an inner cylinder comprising horizontal layers of scaffold material having successively increasing concentrations of the chemotactic agent.

Figure 5A:
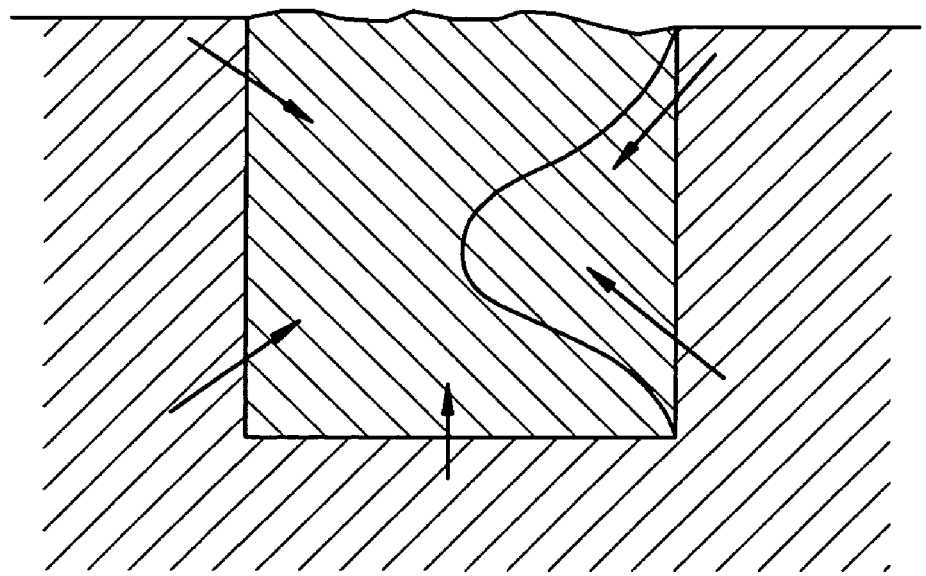

Now referring to FIG. 5a, there is provided a biocompatible implant wherein the chemotactic bioactive agent is graded in the Z-direction. In this embodiment, the chemotactic bioactive agent has a relatively high concentration in the central level of the implant and at a lower concentration near its top and bottom levels. Under these conditions, the cells present near the top and bottom of the implant will be signaled by the chemotactic concentration gradient to migrate towards the central level of the implant, thereby promoting cellular uniformity.

The chemotactic profile of FIG. 5a can be produced by providing multiple slices of scaffold, with each slices having a different chemotactic factor concentration, and arranging those slices horizontally to produce the scaffold.

Figure 5B:
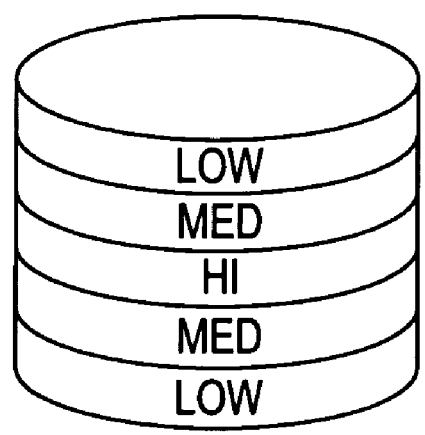

Now referring to FIG. 5b, the chemotactic profile of FIG. 5a can also be produced by providing successive layers of scaffold having increasing bioactive agent concentrations from the bottom to the central region, and then decreasing bioactive agent concentrations from the central to the top region.

In some embodiments, the chemotactic factor is selected from the group consisting of a TGF-$\beta$, a-FGF, b-FGF, PDGF, TNF-$\alpha$, TNF-$\beta$, BMP and GDFs. Preferably, the GDF is GDF-5, more preferably rhGDF-5.

Without wishing to be tied to a theory, it is believed that providing rhGDF-5 as the chemotactic factor in an amount effective to provide an implant concentration of between 10 ng/ml and 5.0 mg/ml would provide the desired chemotactic effect.

Without wishing to be tied to a theory, it is believed that providing TGF-$\beta$ as the chemotactic factor in an amount effective to provide a concentration in the cellular environment of between 2 ng/ml and 1 mg/ml would provide the desired chemotactic effect.

Since chemotaxis is considered to be an early-stage musculoskeletal event, it is preferred that the bioactive agent be available for chemotaxis very early in the repair process. In some embodiments, the bioactive agent is presented to the cellular environment within one day of implantation, more preferably within 12 hours, more preferably within one hour, most preferably substantially immediately.

Since early availability of the chemotactic factor to the cellular environment is desirable, in preferred embodiments, the chemotactic factor is contained in a first phase adapted for a relatively quick release of the chemotactic factor. These phases are described in more detail below in the section describing proliferative factors.

In some instances, enhancing the proliferation of cells may be the primary benefit of a bioactive agent. For example, when an implant already contains a homogeneous distribution activated cells adjacent the porous matrix, the need to supplement natural chemotaxis with a strong chemotactic effector (that would cause an influx of more viable cells into the implant) appears to be low. Similarly, when an implant contains already differentiated cells (such as minced chondrocytes), the need to provide differentiation appears to be low, as the cells are already committed.

Rather, since a slow rehabilitation schedule might prevent the patient from imparting enough motion to the knee to provide sufficient flow of nutrients from the synovial fluid into the implant, there may be a greater need for those activated cells to proliferate throughout the defect. Accordingly, in some embodiments, the implant contains a bioactive agent present in an amount effective to enhance cell proliferation (i.e., a proliferative factor).

In some embodiments, the proliferative factor is selected from the group consisting of a TGF, IGF-I, a-FGF, b-FGF, PDGF, EGF, IL-3, BMPs and GDFs.

Without wishing to be tied to a theory, it is believed that providing rhGDF-5 as the proliferative factor in an amount effective to provide an implant concentration of between 10 ng/ml and 5.0 mg/ml would provide the desired proliferative effect.

Without wishing to be tied to a theory, it is believed that providing TGF-$\beta$ as the proliferative factor in an amount effective to provide an implant concentration of between 2 ng/ml and 10 ng/ml would provide the desired proliferative effect.

Since cell proliferation is considered to be an early-stage musculoskeletal event, it is preferred that the bioactive agent be available for proliferation enhancement fairly early. In some embodiments, the bioactive agent is present in the first phase within 10 days of implantation, more preferably within 5 days, more preferably within one day.

Since early availability of the proliferative factor may be desirable, in preferred embodiments, the proliferative factor is contained in a first phase adapted for a relatively quick release of the proliferative factor. Preferably, the quick release phase is an aqueous phase. In general, an aqueous phase provides quick release because the factor is bound to the aqueous phase via weakly attractive forces such as van der Walls forces and hydrogen bonding.

More preferably, the aqueous phase comprises a hydrogel. Hydrogels may be composed of, but is not limited to, polyacrylates, collagen, elastin, polyethyleneglycol, hyaluronic acid, polyesters or polyacids. Hydrogels are desirable because they bond via weakly attractive hydrogen bonds that provide for an early release of the proliferative factor. In addition, hydrogels are attractive because they provide an adhesive quality that helps retain the implant within the defect; they are capable of being cross-linked in vivo to enhance their strength and their porosity is easily controlled. More preferably, the hydrogel phase is selected from those disclosed in US Published Patent Application No. 2004/0078090, "Biocompatible Scaffolds with Tissue Fragments, published Apr. 22, 2004 ("Binette et al."), the specification of which is incorporated by reference in its entirety.

In some embodiments, the gelation of the hydrogel is accomplished in vivo, and preferably is accomplished by heat-activation, light-activation, free radical-, enzyme-, or other chemical cross-linking, or by combining each part of a two-part system. In some embodiments, the hydrogel phase is contained within the pores of a scaffold material or within granules.

In some embodiments, the bioactive agent is encapsulated in multiple hydrogel capsules or microspheres along with viable cells. This may be accomplished by coating cells in vitro using established methods. This embodiment provides a controlled cellular exposure to the exogenous bioactive agent, so that the appropriate desired signaling of the cells by the bioactive agent may occur in the absence of competing signals.

In some embodiments, controlled release of the bioactive agent from the hydrogel is based upon known degradation of the hydrogel matrix by proteases released in situ.

In some embodiments, the hydrogel selected as the first, early release phase is comprised of collagen. Collagen gels are attractive because they typically can be easily formulated and dispensed; they possess the required adhesive properties for retaining the bioactive agent, and can be designed to degrade quickly. Preferred collagen gels include those disclosed in Binette et al., the specification of which is incorporated by reference in its entirety.

In some embodiments, the aqueous phase comprises hyaluronic acid (HA). HA is desirable because it not only is a suitable carrier for a quick release of a bioactive agent, it is believed that HA also possesses independent therapeutic benefits for osteoarthritis, such as the replenishment of aggrecan. HA is further advantageous because it is a naturally occurring shock absorber and lubricant.

In some embodiments, the first phase containing the chemotactic or proliferative factor is provided as a coating upon a scaffold material. In these embodiments, the coating is generally made of a gel, a film or a degradable polymer. Such a coating is advantageous because it can easily be made by infiltrating the porosity of the scaffold with a liquid.

Since some proliferative bioactive agents (such as some BMP family members like rhGDF-5) are known to solubilize more readily under acidic conditions, then it may be desirable to use a first carrier that produces an acidic environment upon hydrolysis in an amount sufficient to enhance the release of the proliferation factor therefrom.

Without wishing to be tied to a theory, it is believed that many proliferative factors may also function as chemotactic factors as well. Therefore, in some embodiments, providing the proliferative factor in an amount effective to enhance cell proliferation will also enhance chemotaxis.

In some embodiments, the target cells housed within the implant are sufficiently signaled by the native environment to make a sufficient amount of differentiation factor on their own without an exogenous bioactive agent. Accordingly, in some embodiments, simply providing an implant tailored to enhance cellular proliferation and chemotaxis may be sufficient to produce the desired regenerative processes.

For example, in CAIS, minced cartilage tissue that contains chondrocytes is placed into the defect that is in need of cartilage repair/regeneration. These chondrocytes, in addition to acting as a source of cells, may also provide autocrine/paracrine chondrogeneic factors that aid the differentiation of other responding cells that may migrate into the defect. Thus, in this example, it may be beneficial to target the migration and proliferation of the cells into the defect and rely on the chondrogenic factors being produced by the transplanted chondrocytes in the cartilage fragments or existing within the cartilage matrix.

In some implants, there may be a strong need to enhance cell differentiation. For example, when the implant contains a minced layer of chondrocytes, migration of differentiated cells from the minced layer into the porous matrix of the implant may effect a de-differentiation of those cells, and so there appears to be a need for insuring that any reverted cells become chondrocytes. In other implants, the scaffold may be housed with undifferentiated stem cells (obtained from bone marrow or adipose tissue) that have the capacity to differentiate into cells types other than musculoskeletal cell types. In other processes, the scaffold may be implanted with no viable cells and neighboring subchondral bone may be breached in order to obtain undifferentiated stem cells that have the capacity to differentiate into cells types other than musculoskeletal cell types.

Accordingly, in some embodiments, the implant contains bioactive agents present in an amount effective to enhance a desired type of cell differentiation (i.e., a differentiation factor).

In some embodiments, the differentiation factor is selected from the group consisting of a TGF-B, FGFs, BMP, and CDMPs.

Preferably, the CDMP is rhGDF-5. It is known that, when exposed to an effective amount of rhGDF-5, undifferentiated cells will differentiate into musculoskeletal tissues.

Without wishing to be tied to a theory, it is believed that providing rhGDF-5 as the differentiation factor in an amount effective to provide an implant concentration of between 10 ng/ml and 5.0 mg/ml would provide the desired differentiation effect.

Without wishing to be tied to a theory, it is believed that providing TGF-$\beta$ as the differentiation factor at a concentration of approximately 200 ng/ml would provide the desired differentiation effect.

Since cell differentiation is considered to be a fairly late-stage musculoskeletal event, it is preferred that the differentiation factor be available for differentiation enhancement fairly late in the repair process. In some embodiments, the differentiation factor is present in an effective amount at least 10 days after implantation, more preferably after at least 15 days, more preferably after at least 21 days.

Since late availability of the bioactive agent may be desirable, in preferred embodiments, the bioactive agent is associated with a second phase adapted for a relatively late release of the bioactive agent. Preferably, the late release phase is a non-aqueous phase. In general, non-aqueous phases provide late release because the factors are bound thereto by relatively strong forces such as covalent bonds. In preferred embodiments, the second phase material is also a scaffold allowing cellular infiltration.

In some embodiments, the non-aqueous phase comprises a foam. Upon implantation, the bioactive agent is bound to the surface of the foam, and may be in a non-active form. Foams are desirable because their pore size is suitable for cellular infiltration. More preferably, the foam is selected from those disclosed in Binette et al., the specification of which is incorporated by reference in its entirety.

More preferably, the non-aqueous phase comprises a plurality of beads. Beads are desirable because they can be injected and readily mold into any shape, but still have open pores between individual beads for cellular migration. In some embodiments, the bioactive agent is embedded within the beads, while in others, a differentiation factor is present on the surface of the bead. In still others, the agent is both embedded within the beads and is present on the surface of the bead, thereby providing for multiple release profiles of the differentiation factor. More preferably, the bead material is selected from those disclosed in Binette et al., the specification of which is incorporated by reference in its entirety.

In some embodiments, the non-aqueous phase comprises granules having an open porosity. Granules having an open porosity are desirable because the bioactive agent may be both bound to the outer surface of the granule (providing a first release profile) and to the inner surfaces of the granule defined by the open porosity (thereby providing a second release profile). More preferably, the granules are selected from those disclosed in Binette et al., the specification of which is incorporated by reference in its entirety.

In some embodiments, the material selected as the second, later-release phase comprises particulate collagen. Particulate collagen is attractive because it possesses the required stickiness for retaining the bioactive agent for a long time. Preferred (particulate) collagen material include those disclosed in Binette et al., the specification of which is incorporated by reference in its entirety.

In some embodiments, the non-aqueous phase comprises an encapsulant.

It is known that some bioactive agents (such as rhGDF-5) become more soluble as the pH of the cellular environment decreases. Accordingly, in some embodiments, the bioactive agent is bound to a synthetic matrix that produces acid upon hydrolysis. As the matrix degrades, the bioactive agent is slowly released.

Without wishing to be tied to a theory, it is believed that many differentiation agents may also stimulate the mature target cell to produce extracellular matrix (ECM). Therefore, in some embodiments, providing the bioactive agent in an amount effective to enhance cell differentiation will also stimulate ECM production by already differentiated cells as well.

Since ECM production is considered to be a very late-stage musculoskeletal event, it is preferred that the differentiation factor be available for ECM stimulation on a sustained basis. In some embodiments, the differentiation factor is present in an effective amount to stimulation ECM production at least 30 days after implantation, more preferably after at least 60 days, more preferably after at least 90 days.

Since it may sometimes be problematic to effectively bind a desired bioactive agent to a desired scaffold and produce the desired release profiles, in some embodiments, the bioactive agent may be associated with other components of the implant.

In some embodiments, the bioactive agent may be associated with the fibrin glue phase that acts as a carrier for the viable cells. In some embodiments, the bioactive agent-fibrin glue technology disclosed in U.S. Pat. No. 6,054,122 (MacPhee), the specification of which is incorporated by reference in its entirety, is used.

In some embodiments, the bioactive agent may be associated an attachment device (such as a staple) that fixes the scaffold to the native tissue. In some embodiments, the bioactive agent may be attached to the outer surface of the staple. In others, the bioactive agent is embedded in the staple.

It is believed by the present inventors that providing both spatial and temporal variations in the concentration of a bioactive agent will provide a preferred implant even more tailored to provide a desirable environment for musculoskeletal (and more preferably, cartilage) regeneration.

In one preferred embodiment, the implant can be tailored to provide an initial concentration profile that enhances both chemotaxis and proliferation in a first time period (resulting in highly proliferated cells present in a relatively uniform concentration throughout the implant), and then a second concentration profile that enhances differentiation over a second time period (resulting in highly differentiated cells while maintaining a relatively uniform concentration profile throughout the implant).

Figure 6A:
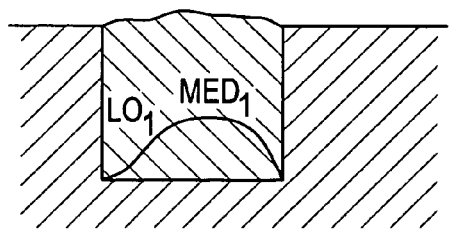
FIGS. 6a-6d depict various implants of the present invention implanted in a musculoskeletal defect, wherein the implants have a first phase providing a spatial concentration gradient and a second phase providing differentiation or ECM stimulation.

Now referring to FIG. 6a, there is provided a biocompatible implant wherein the distribution of the chemotactic agent at a medium concentration ($MED_1$) in its central region and a relatively low concentration ($LO_1$) in its radially peripheral region. Under these conditions, the cells from the neighboring mature tissue will be signaled by the chemotactic concentration gradient to migrate towards the center of the implant, thereby promoting cellular uniformity.

Preferably, the $MED_1$ concentration of the agent not only provides the desired chemotaxis, it also provides a concentration sufficient for cellular proliferation. However, the $MED_1$ concentration is not so high as to promote cellular differentiation.

Figure 6B:
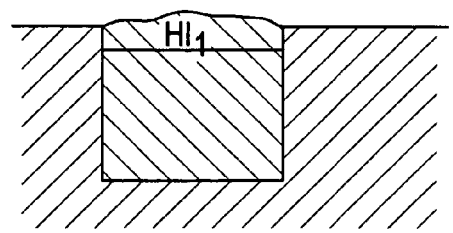

Now referring to FIG. 6b, once the cells have proliferated and are somewhat uniformly present, a previously sequestered bioactive agent is then uniformly released throughout the implant at a uniform high concentration $HI_1$. This $HI_1$ concentration is tailored to produce cellular differentiation of the viable undifferentiated or reverted cells to the mature cell. These target cells will then produce a mature ECM.

Figure 6C:
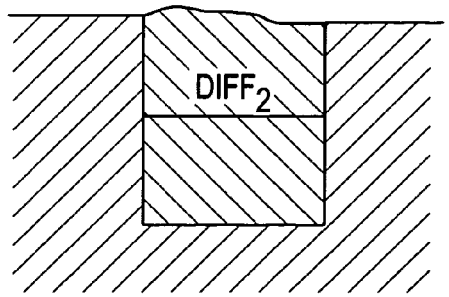

In some embodiments, as in FIGS. 6a-b, the chemotactic/proliferative bioactive agent used in the initial step is the same agent as the differentiation factor used in the second step—the only difference being its concentration. However, the desired chemotaxis/proliferation period followed by a differentiation period can also be achieved with different bioactive agents. For example, in one embodiment, a first bioactive agent may be provided in a manner identical to that described in FIG. 6a to produce cellular proliferation and spatial cellular uniformity. In the second step, and now referring to FIG. 6c, a second bioactive agent can be released through the implant in a concentration $DIFF_2$ known to promote differentiation.

In another embodiment, the proliferation and differentiation agents are present as the same molecule in the same concentration, but simply released at different times.

Figure 6D:
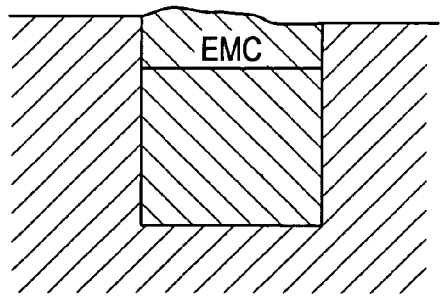

Although the implant of FIGS. 6a and 6b can successfully produce chemotaxis, proliferation and differentiation, there may be a need to stimulate the differentiated cells to produce ECM as well. Accordingly, and now referring to FIG. 6d in some preferred embodiments, the bioactive agent is provided in a concentration that stimulates ECM production as well.

In another embodiment, the proliferation and ECM stimulation agents are present as the same molecule in the same concentration, but simply released at different times.

Figure 6E:
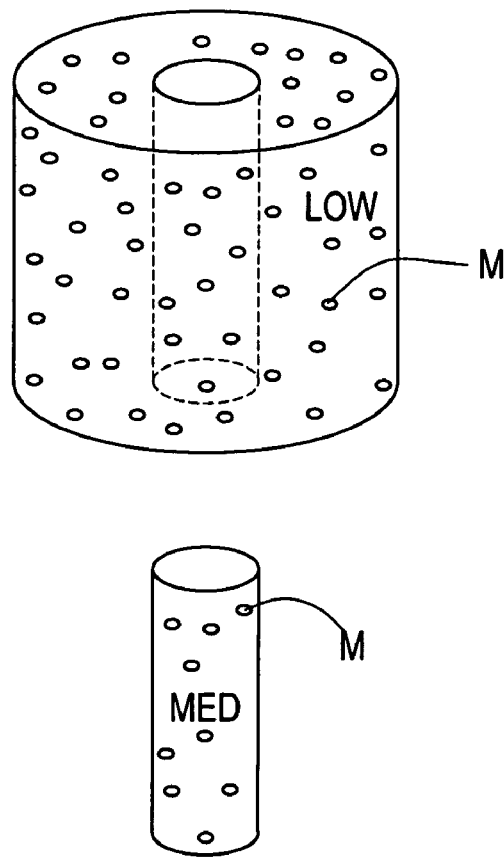
FIGS. 6e-f depict implants of the present invention having a first phase providing a spatial concentration gradient and a second sequestered phase providing differentiation or ECM stimulation.

Now referring to FIG. 6e, the spatial and temporal release shown in FIGS. 6a-6 can be provided by providing an implant comprising:

a) central dowel made of scaffold material and having i) a medium concentration of the bioactive agent freely available throughout the dowel and ii) a high concentration of the bioactive agent sequestered in time-release microspheres M, and b) an outer annulus having i) a low concentration of the bioactive agent freely available throughout the annulus and ii) a high concentration of the bioactive agent sequestered in time-release microspheres M.

In some situations, the surgeon may desire that viable cells move from the bottom to the top of the implant. This may occur if the subchondral bone is purposefully breached to allow the influx of undifferentiated stem cells, or if the implant's bottom surface is coated with a layer of viable cells. In each case, after migration into the bulk of the implant, there may be a need to provide a differentiating bioactive agent to these migrated cells.

Figure 6F:
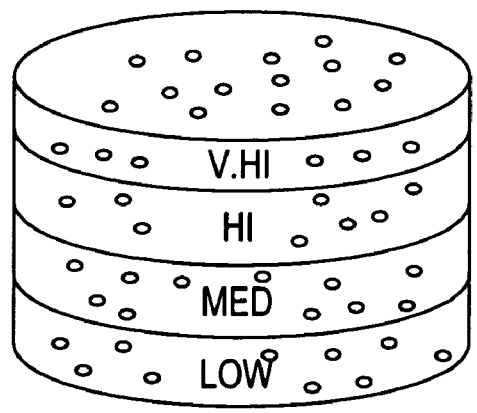

Similarly, and now referring to FIG. 6f, there is provided an implant comprising a plurality of horizontal layers of scaffold material, each layer having i) a successively increasing concentration of the chemotactic bioactive agent freely available throughout the layer, and ii) a high concentration of the differentiating bioactive agent sequestered in time-release microspheres M.

In this case, the successively increasing concentration of the chemotactic agent freely available throughout the implant provides an upward chemotactic signal to the viable cells residing near the bottom of the implant. After migration has occurred, the sequestered differentiating bioactive agent is released, thereby causing the undifferentiated cells or reverted cells to become mature cells.

Figure 7:
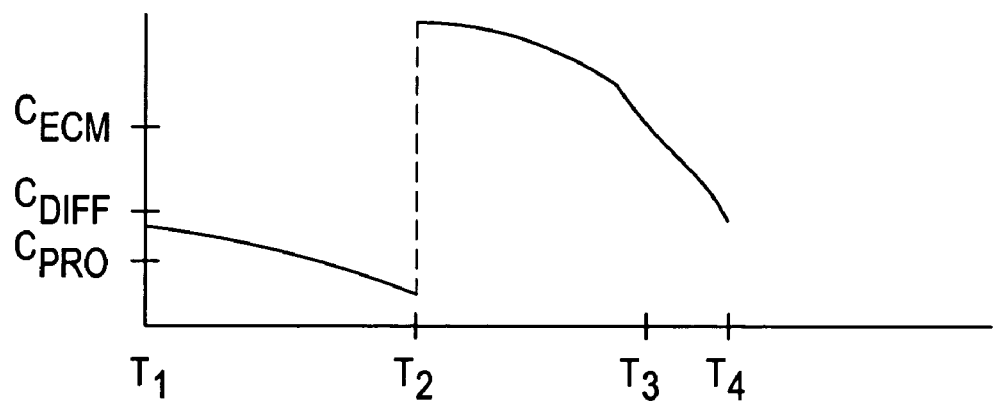
FIGS. 7-8 are graphs of the relative concentrations of a bioactive agent within the cellular environment over time.

Now referring to FIG. 7, in some embodiments using a single agent, the bioactive agent is provided in an initial concentration that stimulates proliferation for a first time period (T1-T2), and then in a second higher concentration that stimulates ECM production for a second time period (T2-T3) and stimulates differentiation for an even longer period (T2-T4).

Although the implant of FIGS. 6a and 6b can successfully produce chemotaxis, proliferation, differentiation and some ECM production, there may be a need to stimulate the differentiated cells to produce ECM on a sustained basis.

Figure 8:
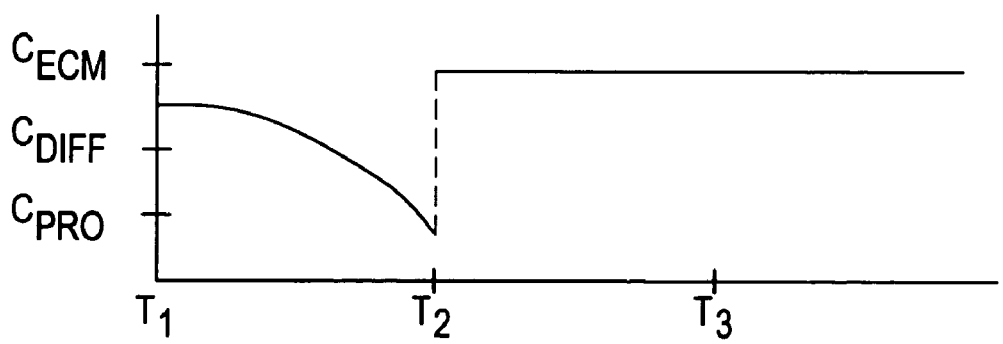

Accordingly, and now referring to FIG. 8, in some preferred embodiments, the time-release vehicle of that releases the differentiating bioactive agent of FIG. 6b can be tailored to provide a sustained release of that factor as well so that its concentration is above $C_{ECM}$ for a sustained period.

In some embodiments, the sustained-release vehicle provides a concentration that stimulates ECM production for at least one month, preferably at least 2 months, more preferably at least 6 months.

Figure 9:
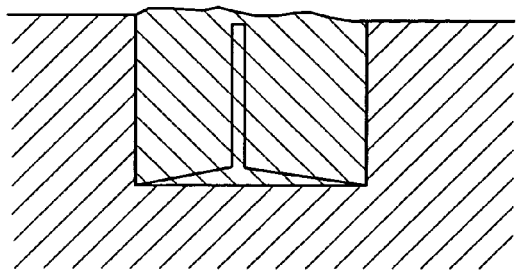
FIG. 9 depicts an implant having a spatially graded concentration profile that provides chemotaxis and a moving front of differentiation to in growing cells.

Now referring to FIG. 9, in some embodiments, the spatial gradient is designed to provide a moving front that induces both chemotaxis and differentiation upon the same cells.

Figure 9A:
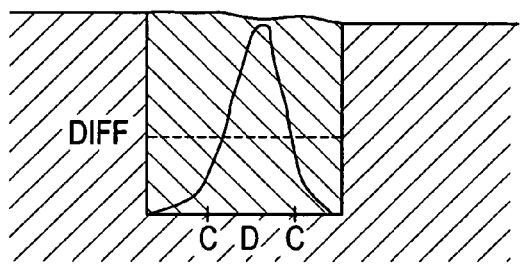
FIGS. 9a-9c depict the moving front of the implant of FIG. 9 over time.

Now referring to FIG. 9a, there is provided an implant having a spatial gradient of a bioactive agent having both chemotactic and differentiation qualities. One such bioactive agent is rhGDF-5. In this FIG. 9a, a relatively sharp spike in the radial center of the implant characterizes the concentration. The concentration of the bioactive agent in the radial center is such that the bioactive agent induces differentiation of the cells residing in this high concentration region. Accordingly, there is a differentiation region D. However, the concentration of the bioactive agent in the radial periphery of the implant is not sufficient to induce differentiation of the cells, but does induce chemotaxis. In this region (called chemotactic influx region C), cells are moving inward from the periphery, thereby enhancing cell homogeneity within the implant.

Figure 9B:
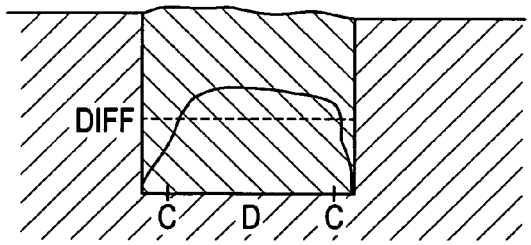

Now referring to FIG. 9b, as time progresses, the concentrated bioactive agent diffuses out thereby widening the differentiation region D. Accordingly, cells that moved into the inner portion of region C during the chemotactic activity of FIG. 9a now stop migrating and differentiate.

Figure 9C:
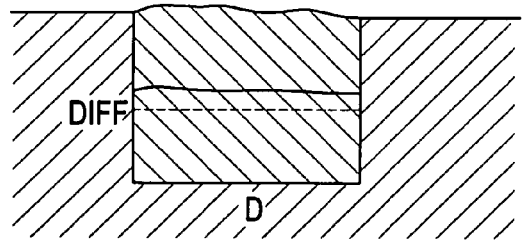
Figure 9D:
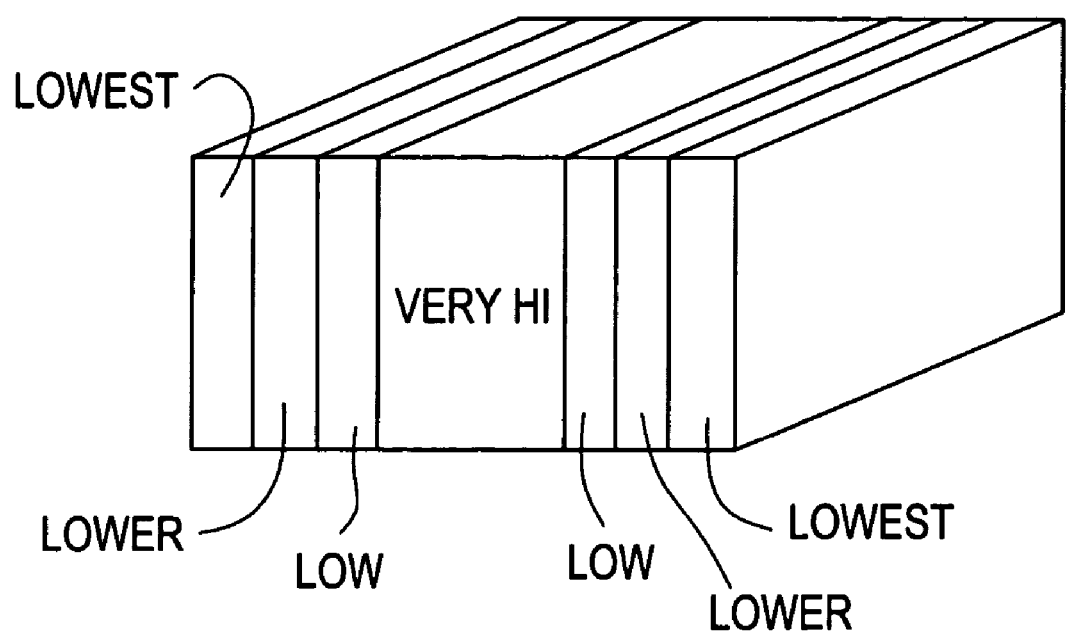
FIG. 9d depicts an implant having a bioactive concentration gradient capable of producing a moving front.

Now referring to FIG. 9c, as time progresses further, the concentrated bioactive agent flattens out to a level in which essentially the entire implant is differentiation region D. Accordingly, cells that moved into the inner portion of region C during the chemotactic activity of FIG. 9b now stop migrating and differentiate.

Now referring to FIG. 9e, the chemotactic profile of FIGS. 9-9c can be produced by providing successive layers of scaffold having increasingly low concentration levels of bioactive agent from the periphery to the central region, and a scaffold layer having a very high bioactive agent concentration in the central region.

This section will describe methods for preparing bioactive gradients for implantable medical devices, and for controlling the release of the bioactive gradients.

A gradual or step gradient of a bioactive agent or mixture of bioactive agents (B) can be prepared at various concentrations and gradient slopes using a variety of means in a variety of matrices (M). For example, the skilled artisan could build the gradient in vitro, fix the gradient to the matrix M, and then implant the device resulting in various release profiles. The skilled artisan could also prepare a device with a homogenous concentration of bioactive agent B and then allow a gradient to form by in vivo mechanisms.

To build a gradient of bioactive agent B in vitro, a variety of gradient-forming means can be utilized. One representative mechanism involves preparing a gradient by selectively mixing different concentrations of bioactive agent B with a matrix M. These separate mixtures could be blended together in a stepwise fashion, as described in FIGS. 1-6. These mixtures could also be prepared in a gradual fashion (non-stepwise) using a "gradient maker", which is commercially available and is currently used for making pH gradient electrophoresis gels. Further, gradual gradients can be prepared by first preparing a stationary phase matrix M in a boyden chamber (which is also commercially available) and allowing bioactive agent B (the mobile phase) to passively diffuse across matrix M. As desired, the diffusion can be stopped when the appropriate gradient profile is achieved. Similarly, the gradient can be created by applying an electric or magnetic field for moving bioactive agent B across matrix M, or by segregating the molecules according to size and charge when bioactive agent B is a mixture). Finally, the gradient can be prepared by dispersing bioactive agent B throughout matrix M by using gravity such as centrifugal forces. All of the above methods would result in gradient formation inside a given matrix M. All of the same methods could be applied in reverse where matrix M is the mobile phase and bioactive agent B is the stationary phase, thereby resulting in gradients of matrix M with a background of bioactive agent B. Also, the above methods could be used to create gradients of both bioactive agent B and matrix M in any configuration such as bioactive agent B present in a high-to-low profile, while matrix M is present in a low-to-high profile, or both bioactive agent B and matrix M are present in low-to-high profiles, and any configuration in between.

Figure 10A:
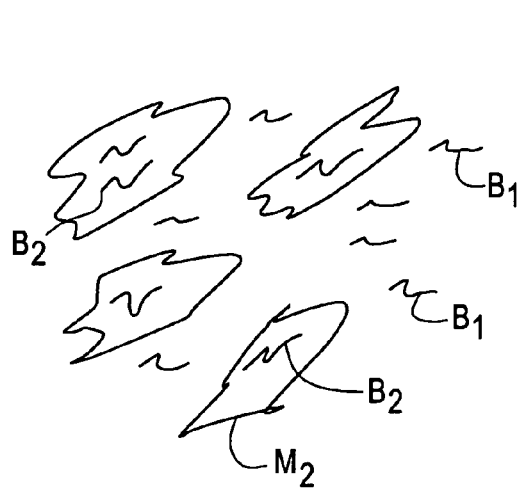
FIGS. 10a-10e present portions of various implants having bioactive agents present in two phases.

In all the cases outlined above, bioactive agent B can be added to matrix M in vitro. It may be further advantageous to fix these mixtures, bioactive agent B to the matrix M, using a variety of means. The fixation of bioactive agent B and matrix M can be achieved by the following as pictured in FIGS. 10-10e Now referring to FIG. 10a, bioactive agent B1 may be present in a hydrogel such as fibrin and so is freely available for presentation upon implantation, while bioactive agent B2 could be physically entrapped in matrix M2 in such a way as B2 would be "encapsulated" in the spaces between molecules in matrix M2 (such as between polymer chains in a networked polymer). In this manner, bioactive agent B2 would not escape from matrix M2 until desired due to physical constraints or steric hindrance.

Figure 10B:
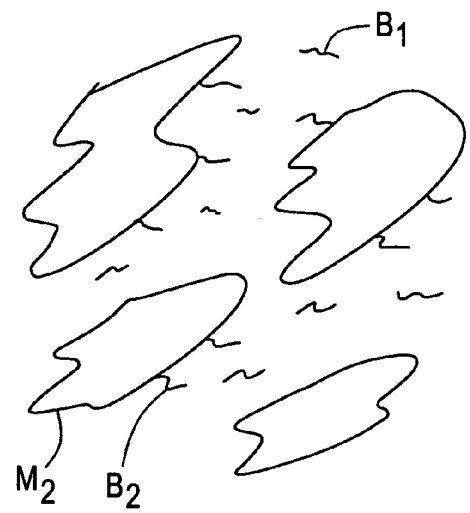

Now referring to FIG. 10b, bioactive agent B1 may be freely available, while bioactive agent B2 could be chemically tethered to matrix M2 using covalent, ionic, or strong hydrogen bonding forces (avidin biotin, for example) using a variety of chemical cross linkers well known in the field. These chemical tethers could be activated using light, free radial initiation, small molecule reaction, temperature, magnetism or electric field after the desired mixture is created as above. Bioactive agent B2 would not escape from matrix M2 until desired due to these chemical forces.

Figure 10C:
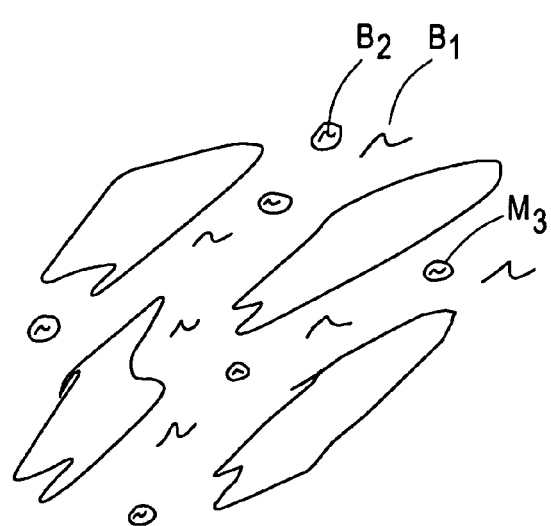

Now referring to FIG. 10c, bioactive agent B1 may be freely available, while bioactive agent B2 could be encapsulated inside another matrix M3 perhaps in sphere format and dispersed throughout the hydrogel in the desired configuration. Bioactive agent B2 would not escape from M3 until desired as it is physically or chemically entrapped inside matrix M3.

Figure 10D:
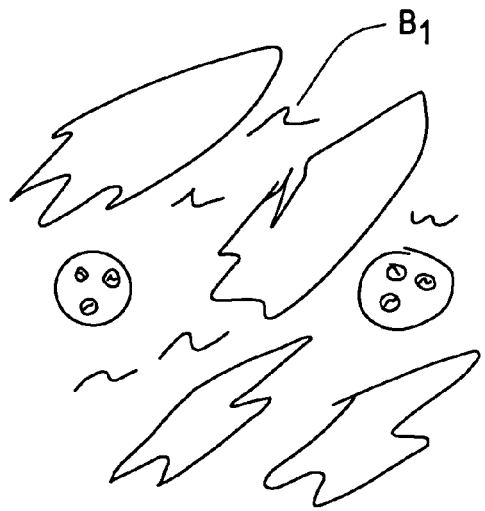

Now referring to FIG. 10d, bioactive agent B1 may be freely available, while bioactive agent B2 could also be chemically bound to the surface of a bead or other carrier inside the M3. Bioactive agent B2 would not escape M3 until desired due to the chemical bond with the carrier and the physical entrapment of M3. All of these mixtures can be applied in reverse as above.

Figure 10E:
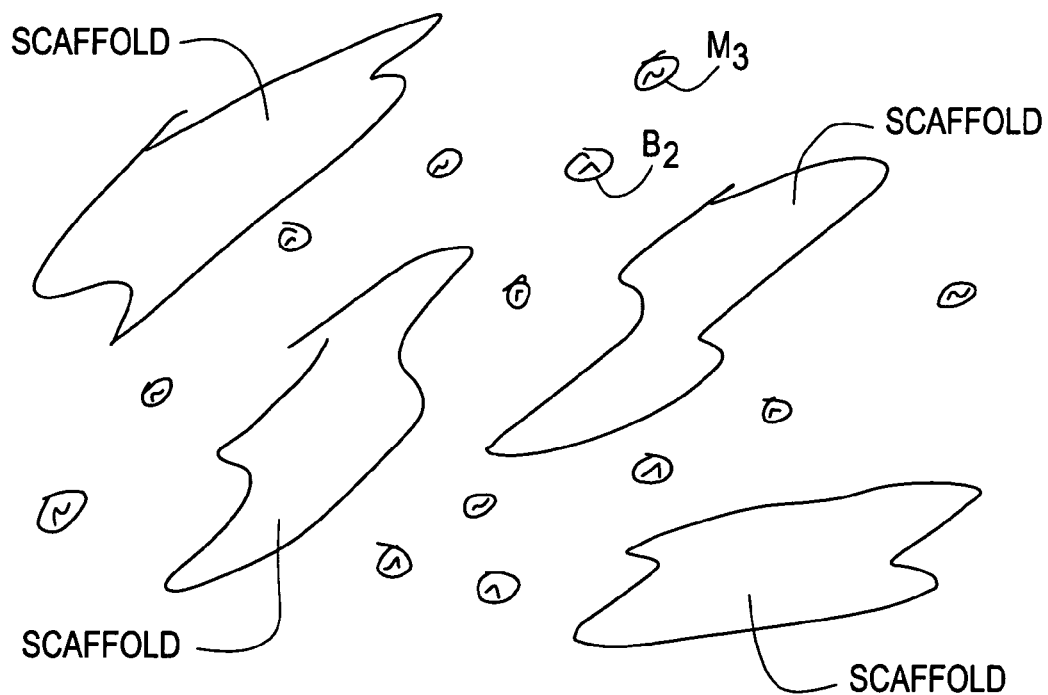

Now referring to FIG. 10e, bioactive agent B2 is encapsulated within matrix M3 to provide sustained release.

After the mixtures of bioactive agent B and matrix M are prepared and fixed, they may (if desired) be released from the matrix using a variety of means. First, if physically entrapped, bioactive agent B can be released by the degradation matrix M, or by the degradation of bioactive agent B to the point where it is small enough to fit through the spaces of matrix M. Matrix M could also be responsive to external electric fields, magnetic fields or mechanical loading (or any combination thereof), which could cause physical distortion of matrix M, thereby releasing bioactive agent B Second, if bioactive agent B is chemically tethered to matrix M, the chemical tethers themselves can be degradable which would then release bioactive agent B. Also, matrix M can degrade, which would also release bioactive agent B, which is attached to part of matrix M but is still bioactive). These tethers could be subject to natural hydrolysis, or enzymatic hydrolysis. Further, the tethers could be released through an addition of another reagent, or by the addition of light, electro or magnetic field or cyclic loading. Third, if bioactive agent B is entrapped inside matrix M2, it can be released through all the mechanisms described above but applied to matrix M2. Fourth, if bioactive agent B is attached to a carrier, it could be released through all the mechanisms described above.

Figure 11:
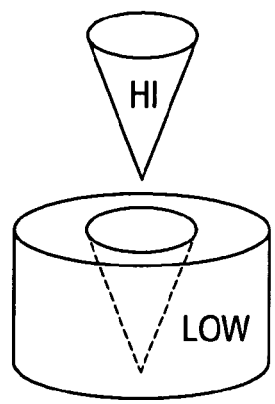
FIG. 11 depicts an exploded view of an implant having a concical shaped concentration gradient.
Figure 12:
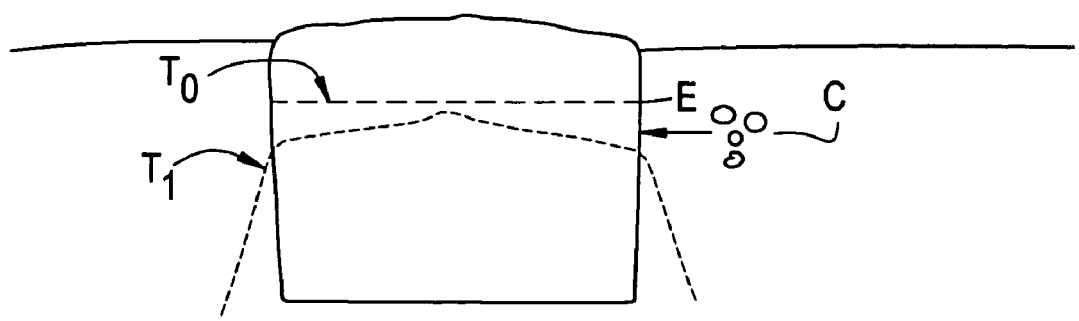
FIG. 12 represents a prior art implant having a homogenous bioactive agent concentration profile.
Figure 13:
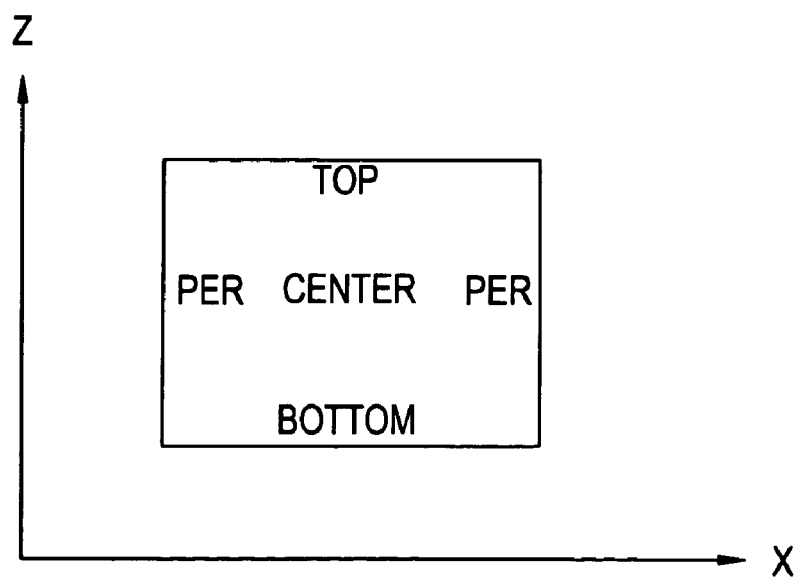
FIG. 13 identifies the terminology used to describe various locations and regions within an implanted implant.

Now referring to FIG. 11, in some embodiments, the assembly of a scaffold having a spatially graded bioactive agent concentration can be provided by using a conical dowel. In this embodiment, the cone also allows for a spatial concentration gradient providing In others, modifying the cylinder to include a Morse taper provides locking of the dowel.

In some embodiments, the implant contains a bioactive agent present in an amount effective to enhance angiogenesis (i.e., an angiogenic factor).

Without wishing to be tied to a theory, it is believed that musculoskeletal regeneration requires both sufficient cellular stimulation and sufficient nutrition for those cells. It is further believed that blood vessels can provide each of stem cells and nutrition to the implant. In addition, white blood cells may also be provided by the blood vessels may beneficially release cytokines that stimulate cellular differentiation.

Accordingly, it may be desirable to provide an angiogenic factor. Since angiogenesis is an early stage event, in some embodiments, providing a bioactive agent in an amount effective to enhance chemotaxis and cellular proliferation will also stimulate angiogenesis as well.

Therefore, in accordance with the present invention, there is provided an implant for repair of an articular cartilage defect, comprising:

a) a matrix, and
b) a cartilage derived morphogenetic protein (such as rhGDF-5) present within the matrix, and
c) an angiogenic factor present within the matrix.

In some embodiments, the implant contains a bioactive agent present in an amount effective to antagonize angiogenesis (i.e., an angiogenic inhibitor).

Without wishing to be tied to a theory, it is believed that angiogenesis is not favorable for a stable articular cartilage phenotype. The induction of new blood vessel formation during angiogenesis could potentially lead to tissue calcification and bone induction. Bone induction in the space normally occupied by articular cartilage could result in osteophyte formation, joint degeneration and pain. The repression of bone induction in the cartilage tissue is believed to be critical for proper performance of the cartilage tissue.

Accordingly, it may be desirable to provide an anti-angiogenic factor. Since angiogenesis is an early stage event, in some embodiments, this factor should be freely available early.

Therefore, in accordance with the present invention, there is provided an implant for repair of an articular cartilage defect, comprising:

a) a porous matrix, and
b) a cartilage derived morphogenetic protein (such as rhGDF-5) present within the matrix, and
c) an anti-angiogenic factor present within the matrix.

It has been reported that rhGDF-5 acts upon cells through two different pathways: the type I/type II BMP receptor-mediated pathway and the ROR2 pathway. Whereas the type I/type II BMP receptor-mediated pathway operates primarily through SMAD signaling molecules to influence cellular activity and differentiation, the ROR2 pathway operates through the MAP kinase signaling molecules, including p38 kinase.

Without wishing to be tied to a theory, it is believed that influencing the p38 pathway (by inhibition, etc.) may have the effect of down regulating one type of cellular activity or differentiation pathway, therefore forcing rhGDF-5 activity through another pathway effectively choosing one cellular activity and/or differentiation pathway over another.

Therefore, in accordance with the present invention, there is provided implant for repair of an articular cartilage defect, comprising:

a) a porous matrix, and b) a cartilage derived morphogenetic protein rhGDF-5 present within the matrix, and c) a P38 inhibitor present within the matrix.

It has been noted by the present inventors that when rhGDF-5 is naturally secreted by native cells, it is essentially immediately bound to the collagen particles adjacent the cell. Despite the immediate binding of rhGDF-5 upon secretion, it is noted that neighboring cells nonetheless respond to this secreted, bound rhGDF-5. Without wishing to be tied to a theory, it is believed that the binding of rhGDF-5 by collagen does not interfere with its subsequent binding to receptors on neighboring cells.

In some embodiments using undifferentiated stem cells may be used as a cell source. The subchondral bone layer adjacent the implant site may be purposefully perforated by the surgeon, thereby allowing stem cells within the bone marrow to enter the matrix of the implant. It is believed that the migration of such stem cells into the matrix occurs rather quickly, thereby obviating the need to supplement the migration with a endogenous chemotactic agent.

Accordingly, in some embodiments, the implant comprises:

a) a biocompatible matrix, b) a first phase containing a differentiation factor, and c) a second phase containing a proliferation factor.

Preferably, the differentiation factor is released relatively quickly from the first phase in order to promote differentiation of the stem cells into mature musculoskeletal cell types. The proliferation factor is then released later from the second phase in order to provide a persistent proliferation stimulus.

In some embodiments, the differentiation and proliferation factors may be the same growth provided in different concentrations or at different times.

In some embodiments, the graft is characterized by a discrete boundary (i.e., no gradient). A discrete boundary in a scaffold includes a first region having a given concentration of a first active agent and a second region immediately adjacent to the first region that has either no active agent or with a second active agent. In this manner, the discrete boundary resembles a step function or a quantum of agent. A discrete boundary graft may be used when it is desirable to obtain a graft having two tissue types adjacent one another without their being integrated with one another. For example, discrete boundaries may be used in grafts to develop new tissue wherein bone tissue is adjacent a nerve, or wherein a blood vessel is surrounded by a different tissue type. Potential orientations for these discrete boundaries are diagrammed in FIGS. 1 to 5.

Figure 14:
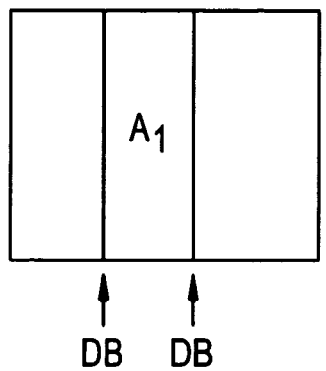
FIG. 14 discloses a graft material wherein the scaffold contains a thin region loaded with an active agent (A1), and this region is bounded on each side by regions in which the scaffold contains no active agent, thereby defining discrete boundaries DB therebetween.

Now referring to FIG. 14, there is provided a graft material wherein the scaffold contains a thin region loaded with an active agent (A1), and this region is bounded on each side by regions in which the scaffold contains no active agent, thereby defining discrete boundaries DB therebetween.

Figure 15:
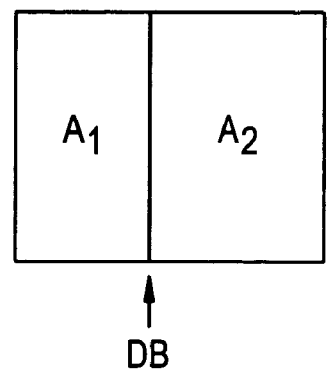
FIG. 15 dscloses a graft material wherein the scaffold contains a first active agent (A1) adjacent a second active agent (A2), thereby defining a discrete boundary DB therebetween.

Now referring to FIG. 15, there is provided a graft material wherein the scaffold contains a first active agent (A1) adjacent a second active agent (A2), thereby defining a discrete boundary DB therebetween.

Figure 16:
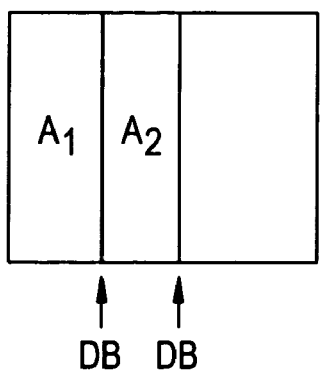
FIG. 16 discloses a graft material wherein the scaffold contains a first active agent (A1) adjacent a thin region of a second active agent (A2), which is adjacent an empty scaffold.

Now referring to FIG. 16, there is provided a graft material wherein the scaffold contains a first active agent (A1) adjacent a thin region of a second active agent (A2), which is adjacent an empty scaffold.

Figure 17:
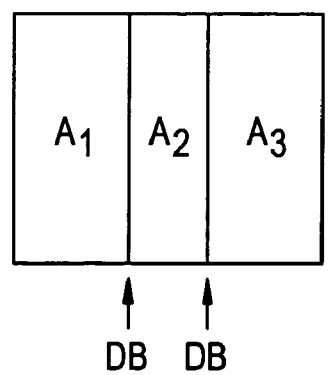
FIG. 17 discloses a graft material wherein the scaffold contains first (A1) and third (A3) active agents separated by a thin region of a second active agent (A2).

Now referring to FIG. 17, there is provided a graft material wherein the scaffold contains first (A1) and third (A3) active agents separated by a thin region of a second active agent (A2).

Figure 18:
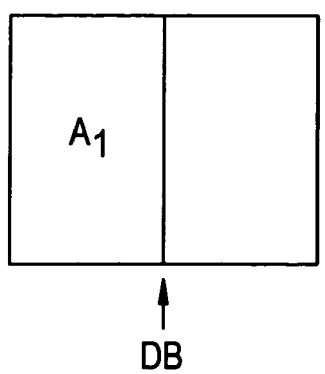
FIG. 18 discloses a graft material wherein the scaffold contains a first active agent (A1) adjacent an empty scaffold.

Now referring to FIG. 18, there is provided a graft material wherein the scaffold contains a first active agent (A1) adjacent an empty scaffold.

Multiple gradients of various active agents on one scaffold can be utilized to develop intermingled tissues with a transition between tissue type A and tissue type B. Any combination of active agents can be used in various combinations allowing for finer control of tissue engineering, the development of a tissue-tissue interface; to influence proliferation and/or differentiation of a tissue, or to influence tissue morphology.

For example, competing gradients can be used to engineer a tendon-bone interface, a tendon-muscle interface, a cartilage-bone tidemark, a influence cartilage layer morphology. This technology can be used in conjunction with other techniques such as altered cell plating density or mechanical-chemical stimulation. FIGS. 6-11 diagram potential orientations for these multiple gradients.

Figure 19:
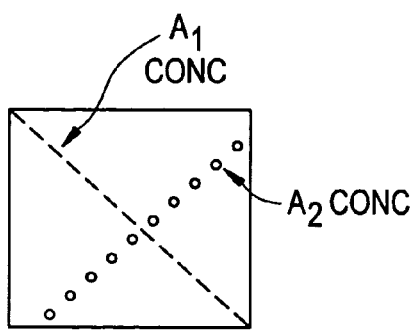
FIG. 19 discloses a scaffold in which active agent 1 (A1) decreases concentration as it progresses from left to right, and this gradient overlaps with active agent 2 (A2), which decreases in concentration as it proceeds from right to left.

Now referring to FIG. 19, there is provided a scaffold in which active agent 1 (A1) decreases concentration as it progresses from left to right, and this gradient overlaps with active agent 2 (A2), which decreases in concentration as it proceeds from right to left.

Figure 20:
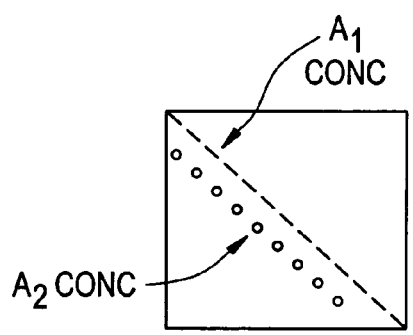
FIG. 20 discloses a scaffold in which each of active agent 1 (A1) and active agent 2 (A2) decrease in concentration as each progresses from left to right.

Now referring to FIG. 20, there is provided a scaffold in which each of active agent 1 (A1) and active agent 2 (A2) decrease in concentration as each progresses from left to right.

Figure 21:
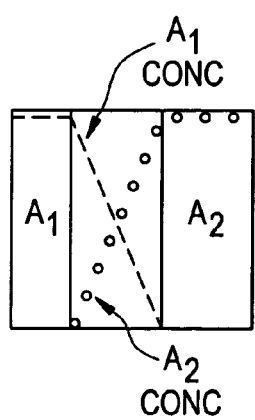
FIG. 21 discloses a scaffold in which each of active agent 1 (A1) and active agent 2 (A2) are each exclusively present within different portions of the graft, and these two portions are separated by a third portion (A1+A2), wherein active agent 1 (A1) decreases concentration as it progresses from left to right, and this gradient overlaps with active agent 2 (A2), which decreases in concentration as it proceeds from right to left.

Now referring to FIG. 21, there is provided a scaffold in which each of active agent 1 (A1) and active agent 2 (A2) are each exclusively present within different portions of the graft, and these two portions are separated by a third portion (A1+A2), wherein active agent 1 (A1) decreases concentration as it progresses from left to right, and this gradient overlaps with active agent 2 (A2), which decreases in concentration as it proceeds from right to left.

Figure 22:
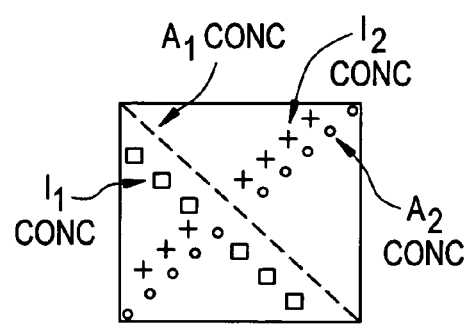
FIG. 22 discloses a scaffold comprising a plurality of active and inhibitory agents in which active agent 1 (A1) promotes bone formation, active agent 2 (A2) promotes tendon formation, inhibitory agent 1 (I1) suppresses tendon formation and inhibitory agent 2 (I2) suppresses bone formation.

Now referring to FIG. 22, there is provided a scaffold comprising a plurality of active and inhibitory agents in which active agent 1 (A1) promotes bone formation, active agent 2 (A2) promotes tendon formation, inhibitory agent 1 (I1) suppresses tendon formation and inhibitory agent 2 (I2) suppresses bone formation.

Figure 23:
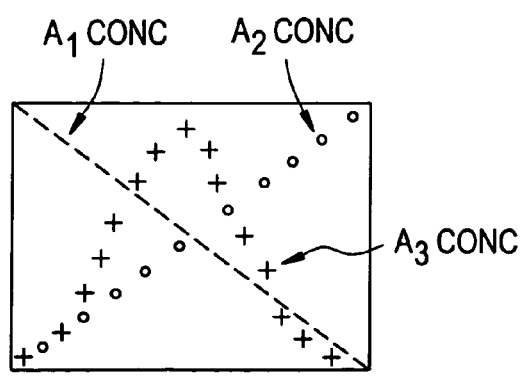
FIG. 23 discloses a scaffold comprising a plurality of active agents arranged in a complex pattern.

Now referring to FIG. 23, there is provided a scaffold comprising a plurality of active agents arranged in a complex pattern.

We claim:

1. An implant for repair of a musculoskeletal defect comprising:

a) a foam matrix having a central region, an upper region, a lower region and a peripheral region, and b) a first bioactive agent present within a first of the regions of the foam matrix, c) a second bioactive agent present within a second of the regions of the foam matrix, wherein the presence of the bioactive agents in different regions of the foam matrix is characterized by different controlled, gradual spatial concentration gradients.

2. The implant of claim 1 wherein at least one of the first and second bioactive agents is a chemotactic bioactive agent.

3. The implant of claim 2 wherein at least one of the spatial concentration gradients promotes cellular migration from native tissue adjacent the defect.

4. The implant of claim 2 wherein at least one of the spatial concentration gradients provides a highest bioactive agent concentration in the central region of the matrix.

5. The implant of claim 2 wherein at least one of the bioactive spatial concentration gradients provides a highest bioactive agent concentration in the peripheral region of the implant.

6. The implant of claim 2 wherein at least one of the bioactive spatial concentration gradients provides a high bioactive agent concentration in the central, upper and lower regions of the matrix and a low bioactive agent concentration in the peripheral region of the implant.

7. The implant of claim 2 wherein at least one of the bioactive spatial concentration gradients provides a highest bioactive agent concentration in the upper region of the matrix.

8. The implant of claim 2 wherein at least one of the bioactive spatial concentration gradients provides a bioactive agent concentration in the central region that is at least 10 times a concentration in the peripheral region.

9. The implant of claim 2 wherein at least one of the spatial concentration gradients provides a high first bioactive agent concentration in the central and peripheral regions of the matrix and a low first bioactive agent concentration in the upper and lower regions of the implant.

10. The implant of claim 2 wherein the second bioactive agent is a differentiation factor.

11. The implant of claim 2 wherein the first and second bioactive agents are different bioactive agents.

12. The implant of claim 10 wherein the first bioactive agent is the same bioactive agent as the second bioactive agent and has a first concentration in the first region, and has a second concentration in the second region.

13. The implant of claim 12 wherein the first bioactive agent is present in the first region in a concentration that avoids differentiation and has a concentration gradient in the second region that promotes cellular migration from native cartilage tissue adjacent the defect.

14. The implant of claim 13 wherein the first bioactive agent is the same bioactive agent as the second bioactive agent and further wherein the first bioactive agent is sequestered for delayed release.

15. The implant of claim 13 wherein the first bioactive agent is a different bioactive agent than the second bioactive agent and is sequestered for delayed release.

16. The implant of claim 10 wherein at least one of the first and second bioactive agents is a differentiation factor that is present in a concentration that stimulates production of extracellular matrix.

17. The implant of claim 10 wherein the differentiation factor is sequestered for delayed release.

18. The implant of claim 10 wherein the chemotactic bioactive agent is adapted for quick release.

19. The implant of claim 2 wherein the controlled, gradual spatial concentration gradients provide chemotaxis and differentiation to the same cell.

20. The implant of claim 2 wherein the bioactive agents are housed in quick and delayed release vehicles.

21. The implant of claim 1 wherein the first bioactive agent promotes bone formation.

22. The implant of claim 21 wherein the second bioactive agent is a chemotactic agent.

23. The implant of claim 22 wherein the first bioactive agent that promotes bone formation is rhGDF-5.

24. The implant of claim 23 wherein the chemotactic agent is TGF-$\beta$.

* * * * *